(12) United States Patent
Benneker et al.

(10) Patent No.: US 7,309,801 B2
(45) Date of Patent: *Dec. 18, 2007

(54) PROCESS FOR TREATING AN AQUEOUS MEDIUM CONTAINING PHOSPHATE, CYCLOHEXANONE AND CYCLOHEXANONE OXIME

(75) Inventors: Arno Benneker, Geleen (NL); Henk Oevering, Elsloo (NL); Johannes Antonius Leonardus Brouwers, St. Joost (NL)

(73) Assignee: DSM IP Assets B.V., Te Heerlen (NL)

( * ) Notice: Subject to any disclaimer, the term of this patent is extended or adjusted under 35 U.S.C. 154(b) by 451 days.

This patent is subject to a terminal disclaimer.

(21) Appl. No.: 10/479,191

(22) PCT Filed: May 29, 2002

(86) PCT No.: PCT/NL02/00342

§ 371 (c)(1),
(2), (4) Date: Jul. 6, 2004

(87) PCT Pub. No.: WO02/096861

PCT Pub. Date: Dec. 5, 2002

(65) Prior Publication Data

US 2005/0038294 A1 Feb. 17, 2005

(30) Foreign Application Priority Data

| May 31, 2001 | (NL) | PCT/NL01/00427 |
| May 31, 2001 | (NL) | PCT/NL01/00428 |
| Dec. 4, 2001 | (EP) | 01204698 |
| Dec. 4, 2001 | (NL) | PCT/NL01/00429 |

(51) Int. Cl.
*C07C 249/08* (2006.01)

(52) U.S. Cl. .................................... 564/259

(58) Field of Classification Search ............ None
See application file for complete search history.

(56) References Cited

U.S. PATENT DOCUMENTS

| 3,720,755 A | 3/1973 | Duyverman et al. |
| 3,720,758 A | 3/1973 | De Rooij et al. |
| 3,862,230 A | 1/1975 | De Rooij et al. |
| 3,940,422 A | 2/1976 | Harita et al. |
| 3,940,442 A | 2/1976 | De Rooij |
| 3,948,988 A | 4/1976 | de Rooij |
| 3,997,607 A | 12/1976 | de Rooij |
| 4,328,198 A | 5/1982 | van de Moesdijk |
| 4,994,613 A | 2/1991 | Fruchey |
| 6,759,556 B2 | 7/2004 | Blaauw et al. |
| 6,844,469 B2 | 1/2005 | Bennecker et al. |

(Continued)

FOREIGN PATENT DOCUMENTS

DE 43 28 795 3/1995

(Continued)

*Primary Examiner*—Yvonne Eyler
*Assistant Examiner*—Yevgeny Valenrod
(74) *Attorney, Agent, or Firm*—Nixon & Vanderhye P.C.

(57) ABSTRACT

The invention relates to a process for treating an aqueous medium containing (i) phosphate and (ii) cyclohexanone and/or cyclohexanone oxime, said process comprising:
feeding the aqueous medium to a stripping zone; passing steam through the aqueous medium in the stripping zone; and
discharging a vapor stream from said stripping zone;
wherein the joint content cyclohexanone and cyclohexanone oxime in the aqueous medium entering the stripping zone is less than 0.08 wt. %.

21 Claims, 2 Drawing Sheets

U.S. PATENT DOCUMENTS

| | | |
|---|---|---|
| 7,005,547 B2 * | 2/2006 | Blaauw et al. ............... 564/259 |
| 2005/0065375 A1 * | 3/2005 | Benneker et al. ........... 564/267 |
| 2006/0079678 A1 | 4/2006 | Oevering et al. |

FOREIGN PATENT DOCUMENTS

| | | |
|---|---|---|
| DE | 4328795 | 3/1995 |
| EP | 0 005291 | 11/1979 |
| GB | 1138750 | 10/1965 |
| GB | 1284515 | 8/1972 |
| WO | 01/94297 | 12/2001 |
| WO | 01/94298 | 12/2001 |

* cited by examiner

PROCESS FOR TREATING AN AQUEOUS MEDIUM CONTAINING PHOSPHATE, CYCLOHEXANONE AND CYCLOHEXANONE OXIME

CROSS REFERENCE TO RELATED APPLICATION

This application is the National Phase of International Application PCT/NL02/00342 filed May 29, 2002 which designated the U.S., and that International Application was published under PCT Article 21(2) in English, which in turn claims priority from PCT/NL01/00427, PCT/NL01/00428, and PCT/NL01/00429, all filed on May 31, 2001.

The invention relates to a process for treating an aqueous medium containing phosphate, cyclohexanone and cyclohexanone oxime. The invention also relates to a process for preparing cyclohexanone oxime.

Oximes can be produced in a process in which a buffered, aqueous medium containing buffer acids or acidic salts, for example phosphate buffers, and buffer salts derived from these acids, is continuously recycled between a hydroxylammonium synthesis zone, in which nitrate or nitrogen oxide is catalytically reduced with molecular hydrogen to hydroxylammonium, and an oximation zone where a ketone, e.g. cyclohexanone, is converted to an oxime. Before the aqueous medium is passed into the hydroxylammonium synthesis zone, it may be enriched with the nitrate by addition of nitric acid or by absorption of nitrous gases in the aqueous medium in which instance nitric acid is formed in situ. After having been enriched in hydroxylammonium in the hydroxylammonium synthesis zone, the aqueous medium is then passed to the oxime synthesis zone, where the hydroxylammonium reacts with a ketone, e.g., cyclohexanone, forming the corresponding oxime. The oxime can then be gseparated from the aqueous medium which is recycled to the hydroxylammonium synthesis zone.

The net chemical reactions occurring during the process can be represented by the following equations:

1) Preparation of the Hydroxylammonium:

$2H_3PO_4 + NO_3^- + 3H_2 \rightarrow NH_3OH^+ + 2H_2PO_4^- + 2H_2O$

2) Preparation of the Oxime

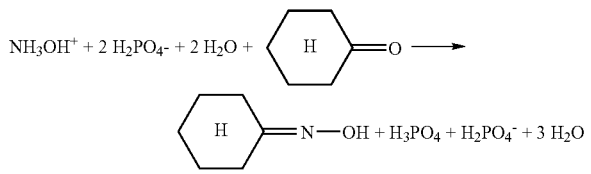

3) Supply of $HNO_3$ to Make Up the Depletion of the Source of Nitrate Ions after Removal of the Oxime Formed

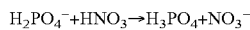

$H_2PO_4^- + HNO_3 \rightarrow H_3PO_4 + NO_3^-$

The reactions to produce the hydroxylammonium and oxime result in the formation of water as a by-product. Besides the water thus formed, water may be introduced into the aqueous medium as a result of a supply of nitric acid in the form of an aqueous solution (e.g. as a 60% aqueous solution of nitric acid). To avoid build-up of water in the aqueous medium, it is desirable to separate water from the aqueous medium.

The catalyst used in the reduction of the nitrate or nitrogen oxide is generally palladium and/or platinum on a carrier material of carbon or alumina. The activity of the catalyst is adversely affected by the presence of organic compounds, in particular ketone and oxime, in the aqueous medium which is passed from the oxime synthesis zone to the hydroxylammonium synthesis zone.

U.S. Pat. No. 3,940,442 describes a process wherein the aqueous medium leaving the oxime synthesis zone comprising phosphate salt, cyclohexanone and cyclohexanone oxime, and having a joint content of cyclohexanone and cyclohexanone oxime of 0.1 wt. % (1000 ppm), is subjected to a stripping step in a column, wherein steam is passed through the aqueous medium such as to reduce the concentration cyclohexanone and cyclohexanone oxime.

It is observed that he process of U.S. Pat. No. 3,940,442 has a high tendency for loss of salt, said salt being entrained in the vapor stream leaving the column. This is disadvantageous since extra salt needs to be added to maintain the desired salt concentration. Moreover the salt entrained in the vapor stream can cause corrosion problems. Furthermore, when the vapor stream is purged, the presence of salt in the vapor stream causes environmental problems.

In view of the above, it is a goal of the invention to provide a process wherein the tendency for salt loss is decreased.

This goal is achieved according to the invention by providing a process for treating an aqueous medium containing phosphate, cyclohexanone and cyclohexanone oxime, said process comprising:
feeding the aqueous medium to a stripping zone; passing steam through the aqueous medium in the stripping zone; and
discharging a vapor stream from said stripping zone;
characterized in that the joint content of cyclohexanone and cyclohexanone oxime in the aqueous medium entering the stripping zone is less than 0.08 wt. %.

The invention also provides a process for preparing cyclohexanone oxime, said process comprising:
passing an aqueous medium containing phosphate from a hydroxylammonium synthesis zone to a cyclohexanone oxime synthesis zone, from the cyclohexanone oxime synthesis zone to a stripping zone and from the stripping zone back to the hydroxylammonium synthesis zone;
in said hydroxylammonium synthesis zone, preparing hydroxylammonium by catalytically reducing nitrate or nitrogen oxide with hydrogen;
in said cyclohexanone oxime synthesis zone, preparing cyclohexanone oxime by reacting hydroxylammonium with cyclohexanone;
passing steam through the aqueous medium in the stripping zone; and
discharging a vapor stream from said stripping zone;
characterized in that the joint content of cyclohexanone and cyclohexanone oxime in the aqueous medium entering the stripping zone is less than 0.08 wt. %.

According to the invention the tendency for salt loss is decreased. According to the invention it is possible to decrease the amount of salt in the vapor stream. It is also possible to increase the superficial gas velocity with no or only limited increase in salt loss. Moreover, the vapor stream can, after condensation, advantageously be used as a wash liquid. The process for preparing cyclohexanone oxime according to the invention has a further advantage that the steam may be obtained by evaporating a quantity of water from the aqueous medium such as to avoid build-up of water in the cycling aqueous medium, and that said quantity of steam is sufficient to obtain low concentrations of cyclohexanone and cyclohexanone oxime in the aqueous medium exiting the stripping zone, without having to re-introduce said evaporated water into the aqueous medium. In the known process of U.S. Pat. No. 3,940,422 part of the evaporated water is, after condensation and separation of organic compounds, re-introduced into the column and into the aqueous medium.

According to the invention the joint content cyclohexanone and cyclohexanone oxime in the aqueous medium entering the stripping zone is less than 0.08 wt. %. Preferably, the joint content cyclohexanone and cyclohexanone oxime in the aqueous medium entering the stripping zone is less than 0.05 wt. %, more preferably less than 0.03 wt. %, in particular less than 0.02 wt. %. Said weight percentages are given with respect to the weight of the aqueous medium. Decreasing the joint content of cyclohexanone and cyclohexanone oxime in the aqueous medium entering the stripping zone has the advantage that the tendency for salt loss is further decreased.

In the stripping zone, steam is passed through the aqueous medium. The aqueous medium and the steam may be contacted by any suitable method. Preferably, the aqueous medium and the steam are contacted in counter current flow. Preferably, the superficial gas velocity of said steam passing through the stripping zone is between 0.2 and 3 m/s, more preferably between 0.4 and 1.5 m/s. As used herein the superficial gas velocity refers to the volumetric steam flow (in m³/s) divided by the free cross sectional area (perpendicular to the direction of steam flow) of the stripping zone (in m²). Applying a superficial gas velocity below the upper preferred values further reduces the tendency for salt loss via the vapor phase. Preferably, the temperature in the stripping zone is between 90-180° C., more preferably between 105 to 160° C. The pressure in the stripping zone may be atmospheric. Preferably, the pressure in the stripping zone is between 0.05 to 1 MPa, more preferably between 0.09 to 0.6 MPa. Preferably, the residence time of the aqueous medium in the stripping zone is between 0.5 and 60 minutes.

The process according to the invention comprises discharging a vapor stream from the stripping zone. The vapor stream comprises steam and organic compounds. Said organic compounds may include organic compounds which were originally present in the aqueous medium prior to entering the stripping zone, e.g. cyclohexanone, and/or organic compounds which are formed in the stripping zone by conversion of cyclohexanone oxime into other products, in particular into cyclohexanone. Typically, the organic compounds include cyclohexanone.

The steam may be obtained from any source, preferably by evaporating part of the water from the aqueous medium. Evaporating part of the water of the aqueous medium may be performed in the stripping zone. It is also possible to evaporate part of the water from the aqueous medium before the aqueous medium enters the stripping zone or after the aqueous medium has been discharged from the stripping zone. In a preferred embodiment, the process comprises obtaining said steam by evaporation of water from the aqueous medium in an amount of 20-400 kg water per m³ of aqueous medium, more preferably in an amount of 50-200 kg water per m³ of the aqueous medium.

Any suitable vessel may be used as a stripping zone. Preferably, the stripping zone is a column. Preferably, such column is a plate column or a packed column. The plate column may be any suitable column fitted with plates, for instance sieve trays, bubble caps or valve trays. Plate columns and packed columns are for instance described in Chemical Engineers' Handbook, by Robert H. Perry and Cecil H. Chilton, 5th edition, international student edition, 1973, McGraw-Hill Kogakusha, Ltd., chapter 18, pages 3-19 (packed columns) and pages 1949 (packed columns).

The aqueous medium contains phosphate, preferably between 2.0-8.0 mol phosphate per liter of aqueous medium. The phosphate may be present as $H_3PO_4$, $H_2PO_4^-$, $HPO_4^{2-}$ and/or $PO_4^{3-}$. Preferably, the aqueous medium is buffered. Preferably, the aqueous medium is an acidic aqueous medium. Preferably, the aqueous medium entering the stripping zone has a pH of between 0 and 4, more preferably between 0.5 and 4. In a preferred embodiment, the aqueous medium entering the stripping zone contains 2.0-8.0 mol phosphate, 0.5-8.0 mol ammonium ($NH_4^+$) and 0.1-5.0 mol nitrate ($NO_3^-$) per liter of aqueous medium. As used herein the phosphate content refers to the joint content of $H_3PO_4$, $H_2PO_4^-$, $HPO_4^{2-}$ and $PO_4^{3-}$ per liter of aqueous medium.

The joint content of cyclohexanone and cyclohexanone oxime in the aqueous medium exiting the stripping zone may be less than 0.02 wt. %. Preferably, the joint content of cyclohexanone oxime and cyclohexanone in the acidic aqueous medium exiting the stripping zone is less than 0.01 wt. %, more preferably less than 0.002 wt. %, in particular less than 0.0005 wt. %, more in particular less than 0.0002 wt. %, most preferably less than 0.0001 wt. %. Said weight percentages are given with respect to the weight of the aqueous medium.

It is found that the vapor stream may, after condensation, advantageously be used as a wash liquid. In a preferred embodiment, the process comprises condensing the vapor stream to obtain a condensed aqueous fluid and washing an organic product with the condensed aqueous fluid. Washing may be carried out by any suitable method wherein the organic product and the condensed aqueous fluid are contacted. Preferably, the condensed aqueous fluid is contacted with the organic product in a mixer, for instance a static mixer or a stirred tank or a column. Said condensing may be carried out by any suitable method, for instance by feeding the vapor stream to a heat exchanger. In a preferred embodiment, the organic product comprises cyclohexanone oxime, preferably dissolved in an organic solvent. Preferably, the process comprises withdrawing the organic product from the cyclohexanone oxime synthesis zone. The process may comprise separating organic compounds from the condensed aqueous fluid prior to said washing. Said separating may be carried out by any suitable method, usually by phase separation.

Preferably, the process comprises separating, preferably extracting, cyclohexanone and cyclohexanone oxime from said aqueous medium, prior to feeding the aqueous medium to the stripping zone. Preferably, the process comprises, prior to feeding the aqueous medium to the stripping zone, extracting cyclohexanone and cyclohexanone oxime from said aqueous medium, such as to reduce the joint content of cyclohexanone and cyclohexanone oxime to a value below 0.08 wt. %, to below 0.05 wt. %, in particular to below 0.03 wt. %, more in particular below 0.02 wt. %. Said extracting may be carried out by contacting the aqueous medium with any suitable solvent. Any suitable organic solvent may be used in which cyclohexanone and cyclohexanone oxime may be dissolved. Preferably, the organic solvent is selected from the group consisting of benzene, toluene, xylene, methylcyclopentane, cyclohexane and mixtures thereof. Most preferably, the organic solvent is toluene. Use may be made of known types of extractors such as for instance an extraction column, or one or more reactors equipped with stirrers, optionally series-connected, each of these reactors also being provided with a liquid-liquid separator. Preferably, a pulsed column, preferably filled with packing bodies is used. Pulsed columns are for instance described in Chemical Engineers' Handbook, by Robert H. Perry and Cecil H. Chilton, 5th edition, international student edition, 1973, McGraw-Hill Kogakusha, Ltd., chapter 21, pages 26-28. The extraction zone is preferably operated at a temperature between 40 and 150° C.

In the cyclohexanone oxime synthesis zone, hydroxylammonium is reacted with cyclohexanone to form cyclohexanone oxime, preferably in the presence of an organic solvent. Any suitable organic solvent may be used in which cyclohexanone and cyclohexanone oxime may be dissolved. Preferably, the organic solvent is selected from the group consisting of benzene, toluene, xylene, methylcyclopentane, cyclohexane and mixtures thereof. Most preferably, the organic solvent is toluene. A suitable process is for instance described in GB-A-1,138,750. In a preferred embodiment, the reaction of hydroxylammonium with cyclohexanone is effected by contacting the aqueous medium and an organic stream comprising cyclohexanone and the organic solvent in countercurrent flow. The cyclohexanone oxime produced may be discharged from the cyclohexanone oxime synthesis zone by any suitable method, preferably by withdrawing an organic product from the cyclohexanone oxime synthesis zone, said organic product comprising the cyclohexanone oxime and the organic solvent. The organic solvent and the cyclohexanone may be introduced into the cyclohexanone oxime synthesis zone at any suitable point, preferably downstream of the point where the organic product is withdrawn from the cyclohexanone oxime synthesis zone (seen in the direction of flow of the aqueous medium). Most preferably, the organic solvent and the cyclohexanone are introduced into the cyclohexanone oxime synthesis zone downstream of the point where the organic product is discharged from the cyclohexanone oxime synthesis zone, and the organic solvent is introduced downstream of the point where the cyclohexanone is introduced into the cyclohexanone oxime synthesis zone (seen in the direction of flow of the aqueous medium. This embodiment has the advantage that extraction of residual amounts of cylohexanone and cyclohexanone oxime is improved. As used herein, the zone between the point where the organic product leaves the cyclohexanone oxime synthesis zone and the point where the cyclohexanone is introduced into the cyclohexanone oxime synthesis zone is also referred to as reaction zone. As used herein the zone between the point where the cyclohexanone is introduced into the cyclohexanone oxime synthesis zone and the point where the organic solvent is introduced into the cyclohexanone oxime synthesis zone is also referred to as extraction zone. For the reaction zone and extraction zone, use may be made of known types of counterflow reactors, such as for instance pulsed columns filled with packing bodies or rotating disc reactors. It is also possible to use a system comprising a number, e.g. 3 to 6, of series-connected reactors equipped with stirrers, each of these reactors also being provided with a liquid-liquid separator. The cyclohexanone oxime synthesis zone is preferably operated at a temperature between 40 to 150° C. Preferably, the reaction medium entering the cyclohexanone oxime synthesis zone has a pH of between 1 and 6, more preferably between 1.5 and 4. Generally, the concentration of hydroxylammonium in the aqueous medium entering the cyclohexanone oxime synthesis zone is between 0.8 and 2.5 mol hydroxylammonium per liter of aqueous medium.

In the hydroxylammonium synthesis zone hydroxylammonium is formed by catalytic reduction of nitrate or nitrogen oxide with hydrogen. The hydroxylammonium synthesis zone may be operated at a temperature ranging from 20 to 100° C., preferably 30-90° C., more preferably 40-65° C., and at atmospheric, sub-atmospheric or elevated pressures, preferably between 0.1 and 5 MPa, more preferably between 0.3 and 3 MPa, and in particular between 0.5 and 2 MPa (hydrogen partial pressure). Preferably, the pH in the hydroxylammonium synthesis zone is between 0.5 and 6, more preferably between 1 and 4. The catalyst employed in this zone is generally present in a range of between 1 to 25 wt. %, preferably between 5 to 15 wt. % of a precious metal, relative to total weight of support plus catalyst. Preferably, the catalyst is a palladium containing catalyst, for instance a palladium or a palladium-platinum catalyst, present on a support, such as for instance carbon or alumina support. Generally, the catalyst is present in the hydroxylammonium synthesis zone in an amount of 0.2-5 wt. % relative to the total liquid weight in the hydroxylammonium reactor vessel (s). The hydroxylammonium synthesis zone is not limited to a specific reactor. A reactor with a mechanical stirrer may be used. Preferably, the reactor is a column, preferably a bubble column. An example of a suitable bubble column is described in NL-A-6908934.

The invention also relates to a process for preparing cyclohexanone oxime, said process comprising:

feeding an aqueous medium containing phosphate and hydroxylammonium to a cyclohexanone oxime synthesis zone;

in said cyclohexanone oxime synthesis zone, preparing cyclohexanone oxime by contacting said aqueous medium with an organic stream comprising cyclohexanone and an organic solvent;

withdrawing an organic product from said cyclohexanone oxime synthesis zone, said organic product comprising cyclohexanone oxime and organic solvent;

washing said organic product with water.

Preferably, the process comprises evaporating part of the water from said aqueous medium, condensing part of the evaporated water and washing the organic product with said condensed water.

DESCRIPTION OF AN EMBODIMENT

Figure 1:
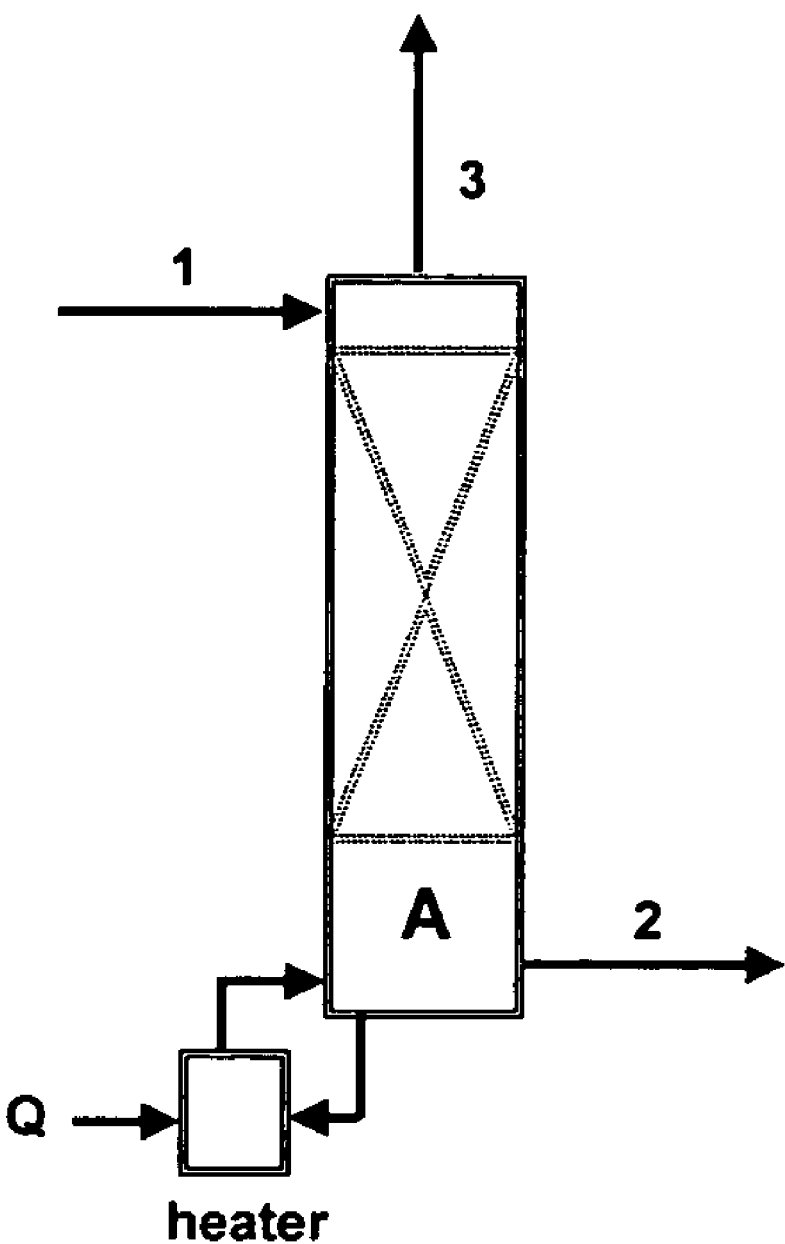
FIG. 1 is a schematic diagram of an embodiment of a stripping column.

Referring to FIG. 1, An aqueous medium containing cyclohexanone and cyclohexanone oxime is fed to stripping zone A (a stripping column) via line 1. The stripped aqueous medium containing a reduced amount of cyclohexanone and cyclohexanone oxime leaves the stripping zone A via line 2. Steam is generated at the bottom of the stripping column by heat supply (Q) via a heater. Steam contacts the aqueous medium in counter current flow and at the top of the column a vapor stream comprising steam and cyclohexanone is discharged through line 3.

Figure 2:
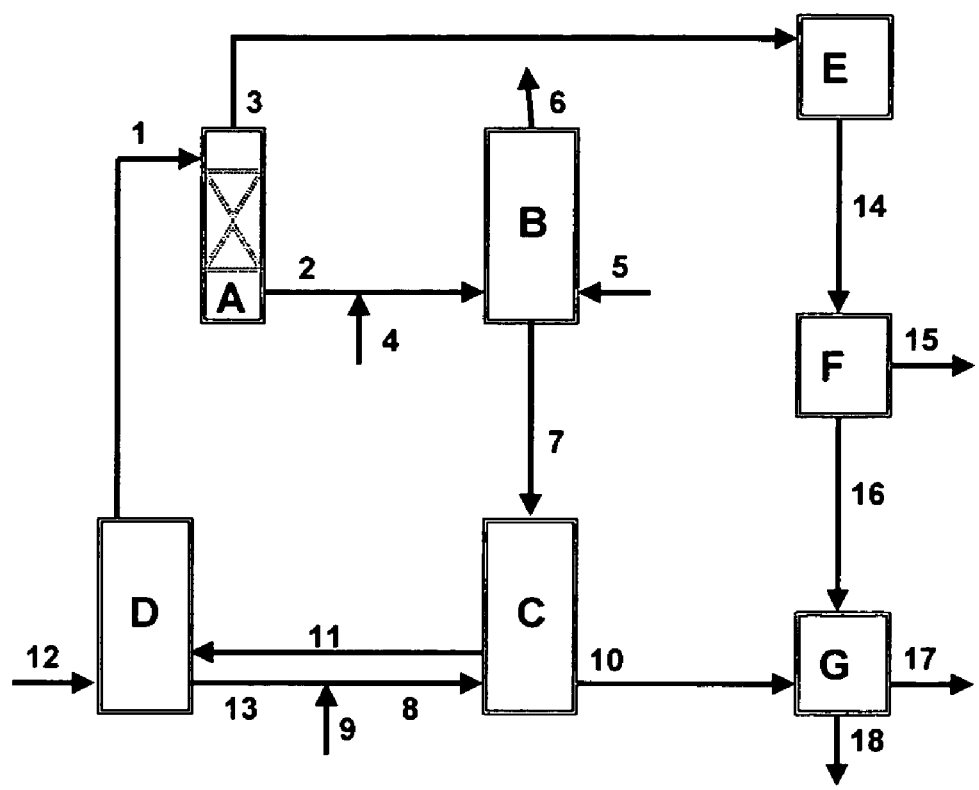
FIG. 2 is a schematic diagram of an embodiment of a process according to the present invention.

Referring to FIG. 2, A represents the stripping zone as described under FIG. 1. The aqueous medium, discharged from the stripping zone A, is recycled to a hydroxylammonium synthesis zone B via line 2. The aqueous medium may be enriched with nitrate ions by addition of nitric acid or absorption of nitrous gases through line 4. In zone B hydroxylammonium is formed by catalytic reduction of nitrate with hydrogen. Hydrogen is fed via line 5 to zone B, containing catalyst and nitrate ions; unreacted hydrogen is discharged, with any other gases, via line 6. After being enriched in hydroxylammonium, in zone B, the aqueous medium is passed to the cyclohexanone oxime synthesis zone via line 7. The cyclohexanone oxime synthesis zone comprises reaction zone C and extraction zone D. The cyclohexanone to be converted into cyclohexanone oxime in zone C is fed to zone C in an organic solvent through line 8. The cyclohexanone is introduced into the organic solvent via line 9. The largest part of cyclohexanone oxime produced and dissolved in the organic solvent is removed from the system via line 10. The aqueous medium is passed from reaction zone C to extraction zone D through line 11. Upon passing reaction zone C, the hydroxylammonium content of the aqueous medium has been reduced by reaction and contains small amounts of cyclohexanone and cyclohexanone oxime. The organic solvent enters extraction zone D through line 12. Within extraction zone D, residual cyclohexanone oxime and cyclohexanone dissolved in an organic solvent is removed from the aqueous medium through line 13. Through line 1, the aqueous medium leaves the extraction zone D to be fed to the stripping zone A, completing the cycle. The process is carried out continuously.

The vapor stream leaving zone A is fed via line 3 to condenser E. Condensed aqueous fluid obtained after condensation leaves condenser E via line 14 and enters separator F. In separator F, organic compounds are separated from condensed aqueous fluid via line 15. The condensed aqueous fluid leaves the separator via line 16 and is fed to washing vessel G to wash organic product comprising cyclohexanone oxime and cyclohexanone which is withdrawn from reaction zone C and enters the washing vessel via line 10. Washed organic product and the used aqueous fluid leave the washing vessel via line 17 and 18 respectively.

The invention will be elucidated by the following examples without being limited thereto.

COMPARATIVE EXPERIMENT A

In this experiment a stripping column is used as indicated in FIG. 1. The stripping column (diameter 2.7 meter, height 18.2 meter) had 21 sieve trays. An aqueous medium withdrawn from an extraction zone as indicated in FIG. 2, was fed to the stripping column at a rate of 93 m$^3$/h. The aqueous medium entering the stripping column had the following composition:
16% by weight of $H_3PO_4$
17% by weight of $NH_4NO_3$
7% by weight of $NH_4H_2PO_4$
0.8% by weight of hydroxylammonium phosphate
joint content of cyclohexanone and cylohexanone oxime: 0.10 wt. % Balance substantially water The stripping column is operated at a pressure of 0.21 MPa and a temperature of 127° C. Steam was generated by evaporating part of the water from the aqueous medium (15 m$^3$/h). Said steam was passed through the column in the opposite direction as the aqueous medium. A vapor stream was discharged from the stripper (15 m$^3$/hr). This stream was condensed, and organic compounds were separated from the condensed aqueous stream. The aqueous phase had a conductivity of 15000 microSiemens/cm (measured using a Mettler DA300 with a Knick 4-POL electrode), corresponding to a loss of 50 mmol phosphate per liter (corresponding to 1764 kg phosphoric acid per day).

EXAMPLE 1

Comparative experiment A was repeated with the only difference that the joint concentration cyclohexanone oxime and cyclohexanone in the aqueous medium entering the column was 0.07 wt. %.

The conductivity of the aqueous phase obtained after condensation of the vapor stream and separation of the organic compounds, was 6000 microSiemens/cm, corresponding to a loss of 18 mmol phosphate per liter (corresponding to 635 kg phosphoric acid per day)

When comparing this example with comparative experiment A, it is seen that the loss of salt is decreased by decreasing the joint content of cyclohexanone and cyclohexanone oxime in the aqueous medium entering the stripping column. Moreover, the conductivity of the condensed vapor phase is decreased, resulting in less corrosion. Furthermore, due to increased purity, the vapor phase is, after condensation more suitable as wash liquid.

EXAMPLE 2

Comparative experiment A was repeated with the only difference that the joint concentration cyclohexanone oxime and cyclohexanone in the aqueous medium entering the column was 0.025 wt. %.

The conductivity of the aqueous phase obtained after condensation of the vapor stream and separation of the organic compounds, was 1400 microSiemens/cm, which corresponds to a loss of 3 mmol phophate per liter (corresponding to 105 kg phosphoric acid per day).

This example shows that a further decrease of the joint concentration cyclohexanone and cyclohexanone oxime in the aqueous medium entering the stripping column, results in a further decrease of the loss of salt and conductivity.

The invention claimed is:

1. Process for treating an aqueous medium containing (i) phosphate and (ii) cyclohexanone and/or cyclohexanone oxime, said process comprising: feeding the aqueous medium to a stripping zone; passing steam through the aqueous medium in the stripping zone; and discharging a vapor stream from said stripping zone; wherein the joint content of cyclohexanone and cyclohexanone oxime in the aqueous medium entering the stripping zone is less than 0.08 wt. %.

2. Process for preparing cyclohexanone oxime, said process comprising: passing an aqueous medium containing phosphate from a hydroxylammonium synthesis zone to a cyciohexanone oxime synthesis zone, from the cyclohexanone oxime synthesis zone to a stripping zone and from the stripping zone back to the hydroxylanimonium synthesis zone; in said hydroxylanimonium synthesis zone, preparing hydroxylammonium by catalytically reducing nitrate or nitrogen oxide with hydrogen; in said cyclohexanone oxime synthesis zone, preparing cyclohexanone oxime by reacting hydroxylammonium with cyclohexanone; passing steam through the aqueous medium in the stripping zone; and discharging a vapor stream from said stripping zone; wherein the joint content of cyclohexanone and cyclohexanone oxime in the aqueous medium entering the stripping zone is less than 0.08 wt. %.

3. Process according to claim 1, wherein the joint content of cyclohexanone and cyclohexanone oxime entering the stripping zone is less than 0.05 wt. %.

4. Process according claim 1, wherein the process comprises, extracting cyclohexanone and cyclohexanone oxime from said aqueous medium, prior to feeding the aqueous medium to the stripping zone.

5. Process according to claim 4, wherein the process comprises, prior to feeding the aqueous medium to the stripping zone, extracting cyclohexanone and cyclohexanone oxime from said aqueous medium, such as to reduce the joint content of cyclohexanone and cyclohexanone oxime to a value below 0.08 wt. %.

6. Process according to claim 5, wherein the process comprises, prior to feeding the aqueous medium to the stripping zone, extracting cyclohexanone and cyclohexanone oxime from said aqueous medium, such as to reduce the joint content of cyclohexanone and cyclohexanone oxime to a value below 0.05 wt. %.

7. Process according to claim 6, wherein said extracting is effected in an extraction column.

8. Process according to claim 7, wherein said extraction column contains packing bodies.

9. Process according to claim 8, wherein said extraction column is a pulsed column.

10. Process according to claim 1, wherein the vapor stream comprises steam and cyclohexanone.

11. Process according to claim 1, wherein the process comprises: condensing the vapor stream to obtain a condensed aqueous fluid; and washing an organic product with the condensed aqueous fluid.

12. Process according to claim 11, wherein the organic product comprises cyclohexanone oxime.

13. Process according to claim 2, wherein the process comprises:
condesing the vapor stream to obtain a concensed aquenous fluid;
withdrawing an organic product comprising cyclohexanone oxime from the cyclohexanone organis synthesis zone; and
washing the organic product with the condensed aquenous fluid after said withdrawing.

14. Process according to claim 1, wherein the superficial gas velocity of the steam in the stripping zone is between 0.2 and 3 M/S.

15. Process according to claim 1, wherein the process comprises obtaining said steam by evaporating water from the aqueous medium.

16. Process according to claim 1, wherein the process comprises obtaining said steam by evaporating 20-400 kg water per m3 of aqueous medium.

17. Process according to claim 1, wherein said stripping zone is a column.

18. Process according to claim 17, wherein said column is a plate column or a packed column.

19. Process according to claim 1, wherein the aqueous medium is an acidic aqueous medium.

20. Process according to claim 19, wherein the aqueous medium entering the stripping zone has a pH of between 0 and 4.

21. Process according to claim 1, wherein the aqueous medium entering the stripping zone contains 2.0-8.0 mol phosphate, 0.5-8.0 mol ammonium and 0.1-5.0 mol nitrate per liter of aqueous medium.

* * * * *